(12) United States Patent
Nardin et al.

(10) Patent No.: US 6,669,945 B1
(45) Date of Patent: Dec. 30, 2003

(54) UNIVERSAL T-CELL EPITOPES FOR ANTI-MALARIAL VACCINES

(75) Inventors: Elizabeth Nardin, Leonia, NJ (US); Alberto Morena, Santafé de Bogotá, CO (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/060,450

(22) Filed: Jan. 21, 1998

Related U.S. Application Data

(60) Provisional application No. 60/033,916, filed on Jan. 21, 1997.

(51) Int. Cl.[7] .................. A61K 38/04; A61K 38/10; A61K 39/015; C07K 7/08; C07K 14/445
(52) U.S. Cl. .................. 424/272.1; 424/191.1; 424/193.1; 530/300; 530/323; 530/326; 530/806; 530/822
(58) Field of Search .................. 424/194.1, 268.1, 424/272.1, 191.1, 185.1, 193.1; 530/300, 323, 326, 806, 822

(56) References Cited

U.S. PATENT DOCUMENTS 5,928,902 A * 7/1999 De Wilde et al. ........ 424/272.1

FOREIGN PATENT DOCUMENTS

| EP | 0 343 460 | 11/1989 | ............ C07K/7/08 |
| WO | 90/11778 | * 10/1990 | |
| WO | 94/25071 | * 11/1994 | |

OTHER PUBLICATIONS

Good et al., Aug. 1986. Genetic control of the immune response in mice to a Plasmodium falciparum sporozoite vaccine. Widespread nonresponsiveness to single malaria T epitope in highly repetitive vaccine. Journal of Experimental Medicine 164: 655–660.*

Rose et al., 1995. A synthetic peptide–based polyoxime vaccine construct of high purity and activity. Molecular Immunology 32: 1031–1037.*

Nardin et al., 1993. T cell responses to pre–erythrocytic stages of malaria: role in protection and vaccine development against pre–erythrocytic stages. Annual Review of Immunology 11: 687–727.*

Nardin et al., *Memorias Do Instituto Oswaldo Cruz Rio De Janeiro,* 87:223–227, 1991.

Moreno et al., *International Immunology,* 3:997–1004, 1991.

Calvo–Calle et al., *Journal of Immunology,* 16:1362–1373, 1997.

Herrera et al., *Infection and Immunity,* 60:154–158, 1992.

Moreno et al., *J. of Immunology,* 151:489–499, 1993.

de Oliveira et al., *Vaccine,* 12:1012–1017, 1994.

Nardin et al., *J. of Immunology,* 146:1674–1678, 1991.

Calvo–Calle et al., *J. of Immunology,* 150:1403–1412, 1993.

* cited by examiner

Primary Examiner—Christopher L. Chin
Assistant Examiner—James L. Grun
(74) Attorney, Agent, or Firm—Darby & Darby

(57) ABSTRACT

The present invention provides methods and compositions for eliciting protective immunity against malaria. In particular, the invention relates to universal T-cell epitopes that elicit T-cell responses in individuals of differing genetic backgrounds. Immunogenic compositions and vaccines including malaria-specific universal T-cell epitopes are disclosed.

24 Claims, 9 Drawing Sheets

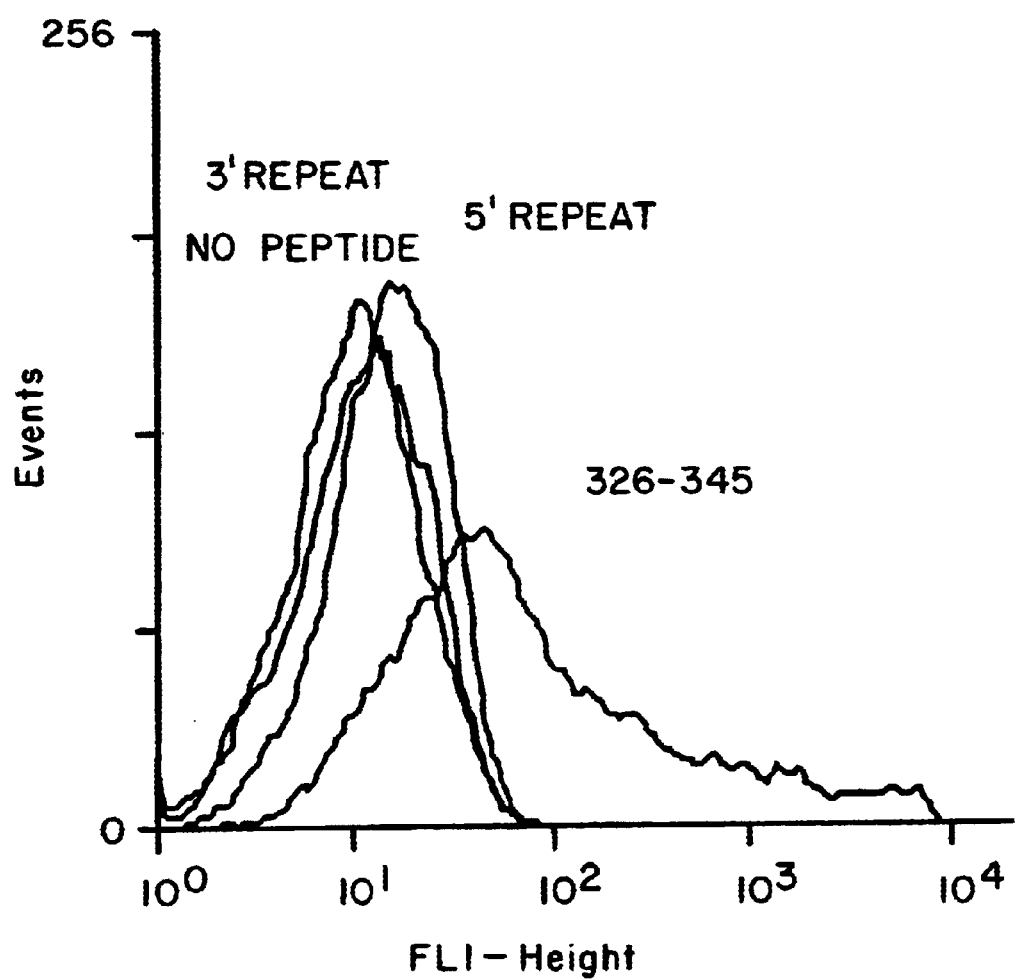

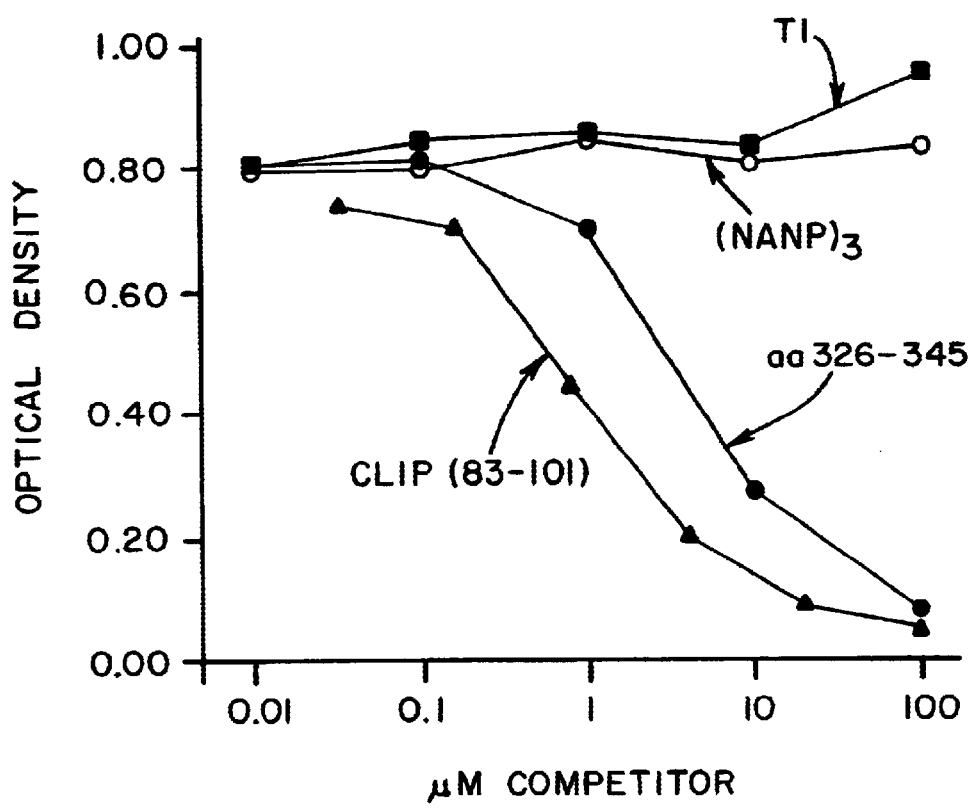

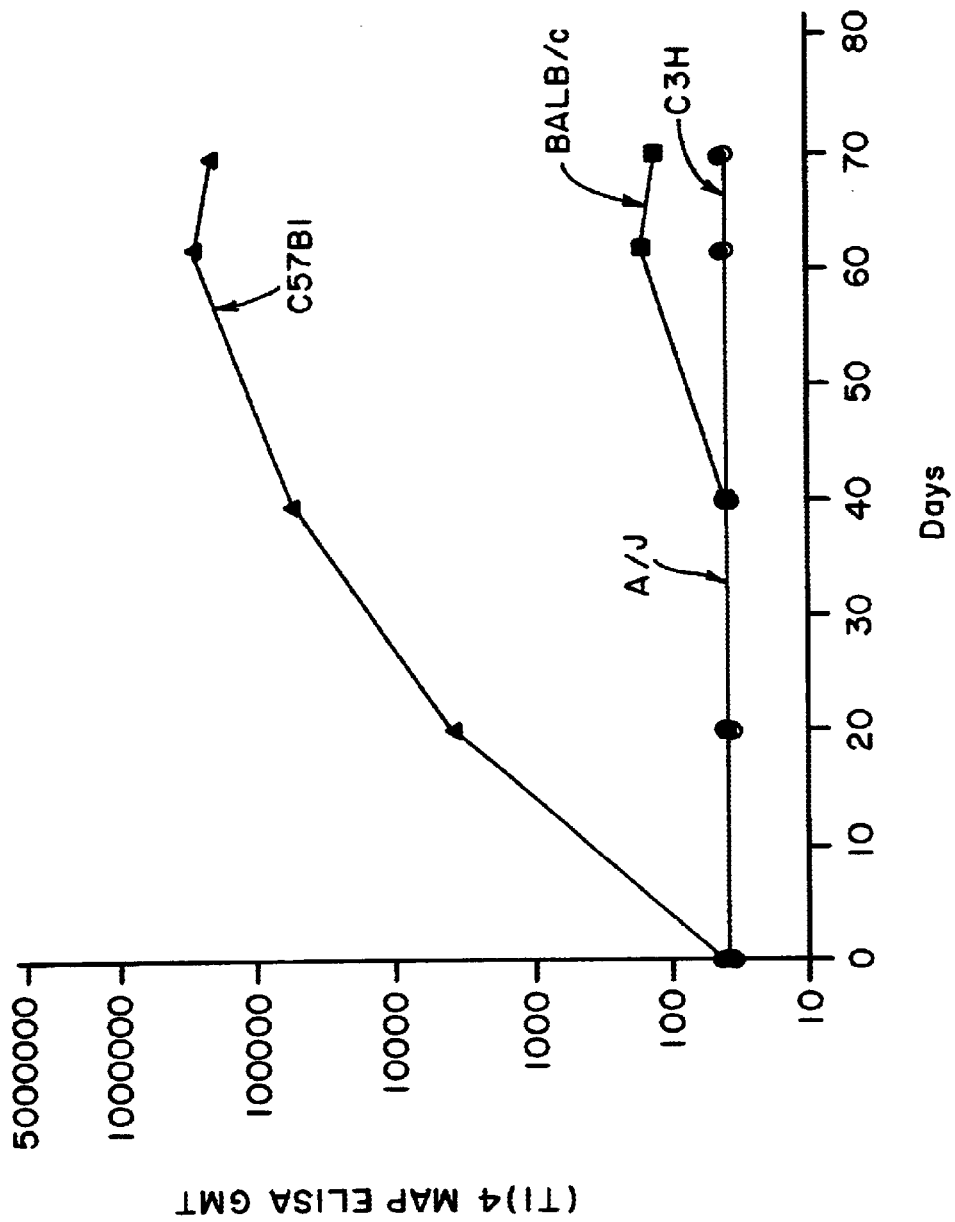

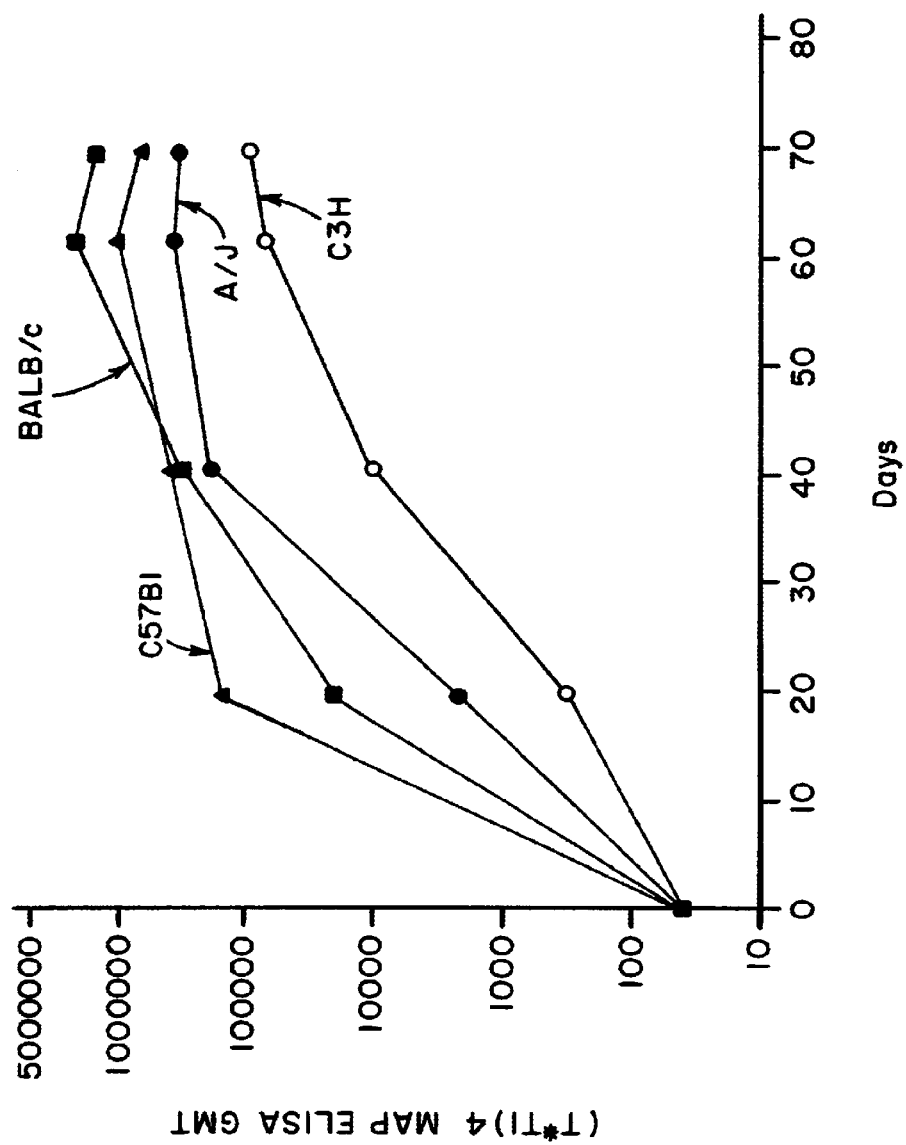

SEQUENCE LISTING

<160> NUMBER OF SEQ ID NOS: 11

<210> SEQ ID NO 1
<211> LENGTH: 12
<212> TYPE: PRT
<213> ORGANISM: P. falciparum

<400> SEQUENCE: 1

Asn Ala Asn Pro Asn Ala Asn Pro Asn Ala Asn Pro
1               5                   10

<210> SEQ ID NO 2
<211> LENGTH: 8
<212> TYPE: PRT
<213> ORGANISM: P. falciparum

<400> SEQUENCE: 2

Asn Val Asp Pro Asn Ala Asn Pro
1               5

<210> SEQ ID NO 3
<211> LENGTH: 20
<212> TYPE: PRT
<213> ORGANISM: P. falciparum

<400> SEQUENCE: 3

Glu Tyr Leu Asn Lys Ile Gln Asn Ser Leu Ser Thr Glu Trp Ser Pro
1               5                   10                  15

Cys Ser Val Thr
            20

<210> SEQ ID NO 4
<211> LENGTH: 16
<212> TYPE: PRT
<213> ORGANISM: P. falciparum

<400> SEQUENCE: 4

Asp Pro Asn Ala Asn Pro Asn Val Asp Pro Asn Ala Asn Pro Asn Val
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Poly-alanine peptide containing DR 1, 4, 7 and
      13 allele specific binding motifs for use as indicator peptide.

<400> SEQUENCE: 5

Gly Phe Lys Ala Ala Ala Ala Ala Ala Ala
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Poly-alanine peptide containing DR 3 allele
      specific binding motifs for use as indicator peptides.

<400> SEQUENCE: 6

Ile Ala Tyr Asp Ala Ala Ala Ala Ala
1               5

<210> SEQ ID NO 7
<211> LENGTH: 10
<212> TYPE: PRT
<213> ORGANISM: Artificial Sequence
<220> FEATURE:
<223> OTHER INFORMATION: Poly-alanine peptide containing DR 8 allele
      specific binding motifs for use as indicator peptide.

<400> SEQUENCE: 7

Gly Tyr Arg Ala Ala Ala Ala Ala Ala Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: UD4 peptide containing DR 4 allele specific
      binding motifs for use as indicator peptide.

<400> SEQUENCE: 8

Tyr Pro Lys Phe Val Lys Gln Asn Thr Leu Lys Ala Ala
1               5                   10

<210> SEQ ID NO 9
<211> LENGTH: 36
<212> TYPE: PRT
<213> ORGANISM: Artificial Sequence
<220> FEATURE:
<223> OTHER INFORMATION: Fusion of Carboxyl Terminus of SEQ ID NO:4 to
      Amino Terminus of Seq ID NO: 3, designated T*T1

```
<400> SEQUENCE: 9

Glu Tyr Leu Asn Lys Ile Gln Asn Ser Leu Ser Thr Glu Trp Ser Pro
1               5                   10                  15

Cys Ser Val Thr Asp Pro Asn Ala Asn Pro Asn Val Asp Pro Asn Ala
            20                  25                  30

Asn Pro Asn Val
        35

<210> SEQ ID NO 10
<211> LENGTH: 28
<212> TYPE: PRT
<213> ORGANISM: Artificial Sequence
<220> FEATURE:
<223> OTHER INFORMATION: Fusion of Carboxyl Terminus of SEQ ID NO:4 to
      Amino Terminus of Seq ID NO: 1, designated T1B

<400> SEQUENCE: 10

Asn Ala Asn Pro Asn Ala Asn Pro Asn Ala Asn Pro Asp Pro Asn Ala
1               5                   10                  15

Asn Pro Asn Val Asp Pro Asn Ala Asn Pro Asn Val
            20                  25

<210> SEQ ID NO 11
<211> LENGTH: 48
<212> TYPE: PRT
<213> ORGANISM: Artificial Sequence
<220> FEATURE:
<223> OTHER INFORMATION: Fusion of Amino Terminus of SEQ ID NO: 4 to
      Carboxyl Terminus of SEQ ID NO: 3 with Concomitant Fusion of
      Carboxyl Terminus of SEQ ID NO:4 to Amino Terminus of
      Seq ID NO: 1, designated T1BT*

<400> SEQUENCE: 11

Asn Ala Asn Pro Asn Ala Asn Pro Asn Ala Asn Pro Asp Pro Asn Ala
1               5                   10                  15

Asn Pro Asn Val Asp Pro Asn Ala Asn Pro Asn Val Glu Tyr Leu Asn
            20                  25                  30

Lys Ile Gln Asn Ser Leu Ser Thr Glu Trp Ser Pro Cys Ser Val Thr
        35                  40                  45
```

UNIVERSAL T-CELL EPITOPES FOR ANTI-MALARIAL VACCINES

This application claims priority pursuant to 35 U.S.C. §119 from provisional application Serial No.60/033,916, filed Jan. 21, 1997, the disclosure of which is hereby incorporated herein by reference in its entirety.

FIELD OF THE INVENTION

This invention relates to vaccines effective in eliciting protective immunity against malaria, in particular vaccines comprising universal T-cell epitopes that elicit T-cell responses in individuals of differing genetic backgrounds.

BACKGROUND OF THE INVENTION

The public health problems caused by malaria, which currently infects 400–500 million individuals world-wide, have been exacerbated by the emergence of multi-drug resistant parasite strains and insecticide-resistant mosquito vectors. These developments have led to increased efforts to provide an effective vaccine to prevent the mortality and morbidity due to malaria, in particular *P. falciparum*, the most virulent of the Plasmodial species.

In a mammalian host, malaria infection is initiated by the motile sporozoite stage of the organism, which is injected into the circulation by the bite of infected mosquitoes. The sporozoite is targeted to the host's liver cells through interaction of a major component of the sporozoite surface membrane, the circumsporozoite (CS) protein, with specific receptors on the hepatocyte surface. Following intracellular multiplication and release from ruptured hepatocytes, the parasites invade red blood cells and initiate the malaria erythrocytic cycle; this phase of infection is responsible for clinical disease and, in the case of *P. falciparum*, may be lethal.

A major focus of malaria vaccine development has been the CS protein, which is present in both sporozoite and liver stages of the parasite. Polyclonal and monoclonal antibodies specific for an immunodominant B-cell epitope within the repeat region of the CS protein, the $(NANP)_3$ peptide SEQ ID NO:1, neutralize the infectivity of sporozoites of rodent, primate and human malaria species (Nardin et al., *J.Exp.Med.* 156:20, 1982). Use of the $(NANP)_3$ peptide in a vaccine, however, resulted in only a limited immune response, most probably due to low epitope density and/or lack of a suitable T-cell epitope (Herrington et al., *Nature* 328:257, 1987).

The present inventors have defined parasite-derived T-cell epitopes using CD4+ T-cell clones derived from four human volunteers immunized by repeated exposure to the bites of irradiated *P. falciparum* malaria infected mosquitoes. When three of these volunteers were challenged with infective *P. falciparum* sporozoites, they were protected against malaria, as shown by the total absence of blood stage infection (Herrington et al., *Am.J.Trop.Hyg.* 45:535, 1991).

Using CD4+ T-cell clones derived from these sporozoite immunized volunteers, two T-cell epitopes have been identified, one located in the repeat region and one in the C-terminus of the *P. falciparum* CS protein. The T-cell epitope contained in the $NH_2$-terminal repeat region, termed T1, consists of alternating NVDPNANP repeats SEQ ID NO:2 (Nardin et al., *Science* 246:1603, 1989). The T1 epitope is contiguous to, but antigenically distinct from, the COOH-terminal repeat region which contains the $(NANP)_3$ B cell epitope. The human CD4+ T-cell clones that specifically recognize peptides derived from various combinations of the $NH_2$-terminal repeat region and that contain NVDPNANP do not respond to the $(NANP)_3$ repeat peptide. The T1 repeat epitope is conserved in all *P. falciparum* isolates sequenced thus far and therefore its inclusion in a vaccine is expected to induce immune responses reactive with parasites of diverse geographical regions.

The second T-cell epitope identified by sporozoite-specific human CD4+ T-cell clones is contained in a peptide spanning amino acid residues numbered 326–345, EYLNKIQNSLSTEWSPCSVT, SEQ ID NO:3 of the *P. falciparum* NF54 strain CS protein (Moreno et al., *Int.Immunol.* 3:997, 1991; Moreno et al., *J.Immunol.* 151:489, 1993). This epitope was shown to be recognized by cytotoxic and non-cytotoxic class II-restricted human CD4+ T-cell clones and class I-restricted CD8+ CTL.

The 326–345 amino acid sequence is unique in that it overlaps both a polymorphic, as well as a conserved region, RII (Dame et al., *Science* 225:593, 1984), of the CS protein. The conserved RII-plus contains a parasite ligand that interacts with hepatocyte receptors to initiate the intracellular stage of the malaria life cycle. The peptide-specific human CD4+ T-cells recognize a series of epitopes within the 326–345 peptide, all of which overlap the conserved RII found in the CS protein of all *Plasmodium* species.

The fact that the T* epitope was defined by CD4+ T-cells derived from human volunteers immunized by multiple exposures to the bites of malaria-infected mosquitoes suggests that this peptide sequence is efficiently processed for presentation by HLA class II molecules following exposure to the native CS protein on the sporozoite. It is contemplated that vaccines containing this parasite-derived T-cell epitope can elicit anamnestic responses in naturally-infected individuals and can provide for vaccine-induced immunity to be maintained by continued exposure to the parasite under natural conditions.

Class II-restricted CD4+ T-cells play a central role in the induction of both cellular and humoral immunity to the pre-erythrocytic stages of the malaria parasite (Nardin et al., *Ann.Rev.Immunol.* 11:687, 1993). If the T-cell epitopes contained within a synthetic malaria vaccine bind to only a limited range of class II molecules, the vaccine may fail to elicit immune responses in individuals of diverse genetic backgrounds. Earlier studies have shown that the (NANP) repeats of the *P. falciparum* CS protein induced low or undetectable T-cell responses in naturally-infected individuals living in malaria endemic areas (Herrington et al., *Nature* 328:257, 1987; Etlinger et al., *J.Immunol.* 140:626, 1988; Good et al., *Proc.Natl.Acad. Sci. USA* 85:1199, 1988).

Thus, there is a need in the art for parasite-derived T-cell epitopes that bind to most, if not all, class II molecules for inclusion in immunogenic compositions and vaccines, to provide protective immunity against malaria in individuals of diverse genetic backgrounds.

BRIEF DESCRIPTION OF THE DRAWINGS

FIG. 1A is a histogram of the fluorescence obtained by incubation of EBV-B 9008 cells with biotinylated peptides. FIG. 1B is a histogram of the fluorescence obtained by incubation of EBV-B 9065 cells with biotinylated peptides.

FIG. 2A is a graphic illustration of peptide competition ELISA using DR4(DRB1*0401) class II molecules. Varying concentrations of competitor peptides 326–345, T1 or $NANP_3$ were tested for their ability to inhibit binding of a biotinylated indicator peptide $GFK(A)_7$ to the soluble DR molecules. The peptide/MHC complexes were captured on anti-DR Mab-coated ELISA plates and revealed by incubation with HRP-avidin and peroxidase substrates. FIG. 2B is a graphic illustration of peptide competition ELISA using DR 13 (DRB1*1301) class II molecules, performed as described for FIG. 2A.

Figure 2A:
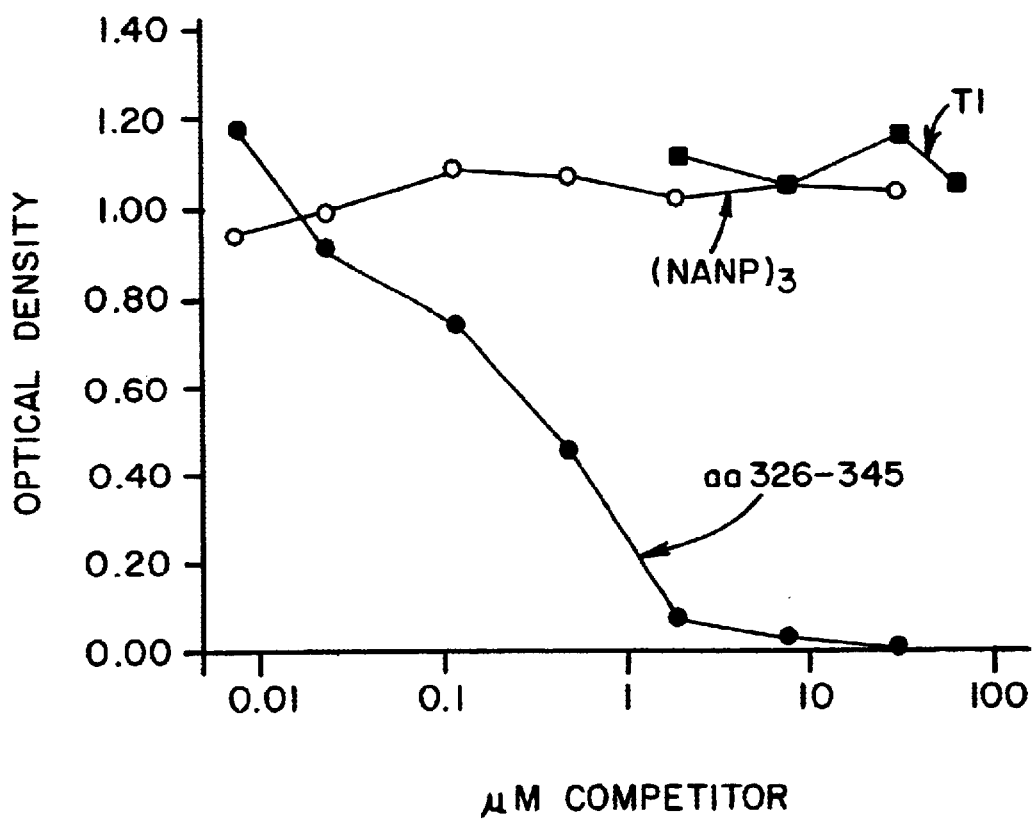
Figure 2B:
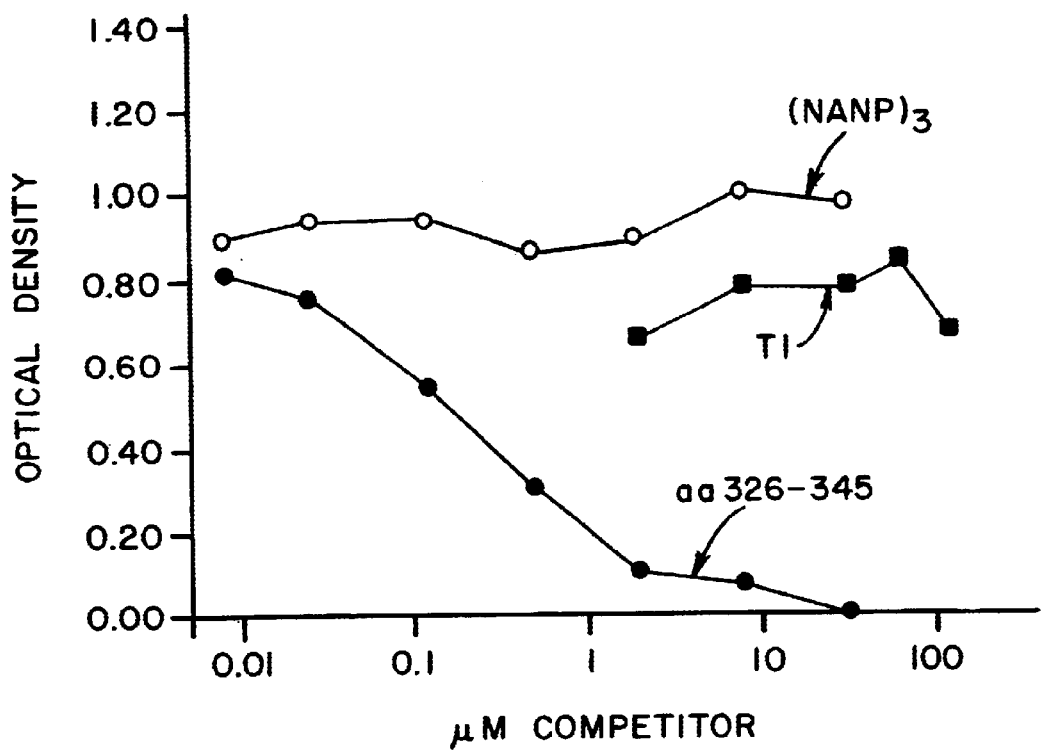
Figure 3B:
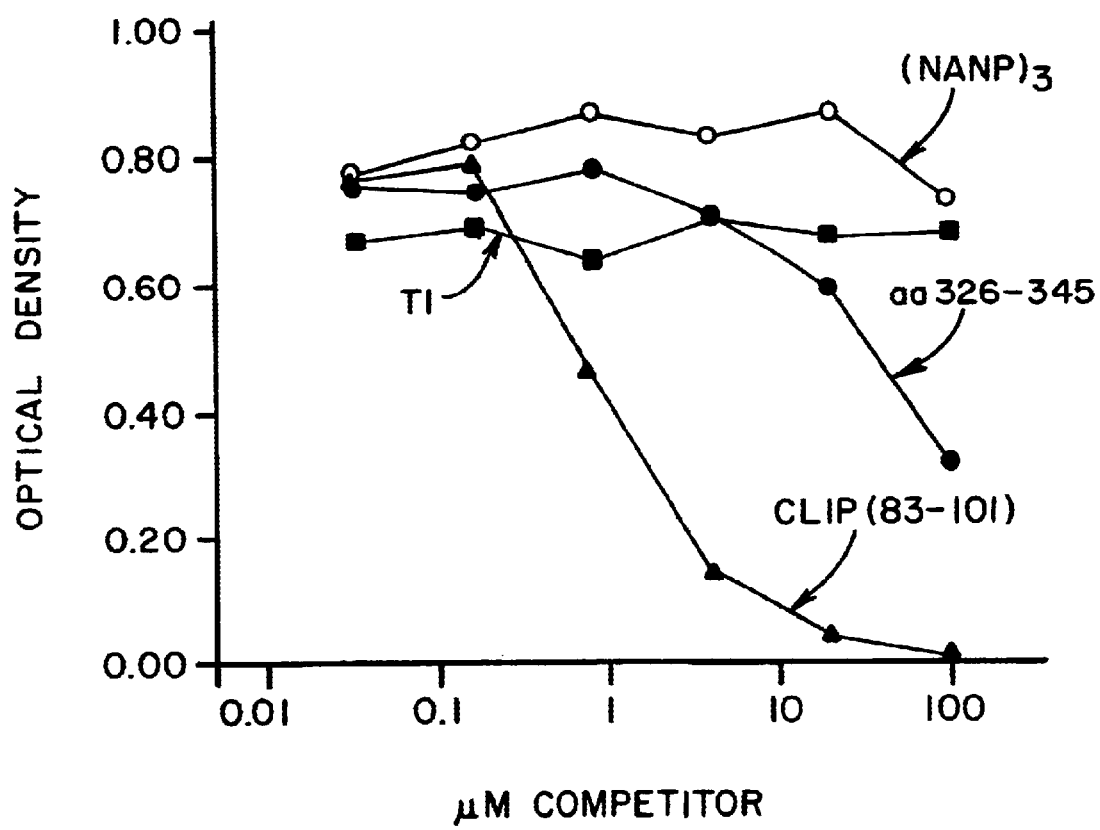

FIG. 3A is a graphic illustration of a peptide competition assay using soluble DQ 9 (DQ A1*0201/DQ B1*0303) class II molecules carried out as described for FIG. 2A. FIG. 3B is a graphic illustration of a peptide competition assay using soluble DQ 7 (DQ A1*0501/DQ B1*0301) class II molecules carried out as described for FIG. 2A.

Figure 4B:
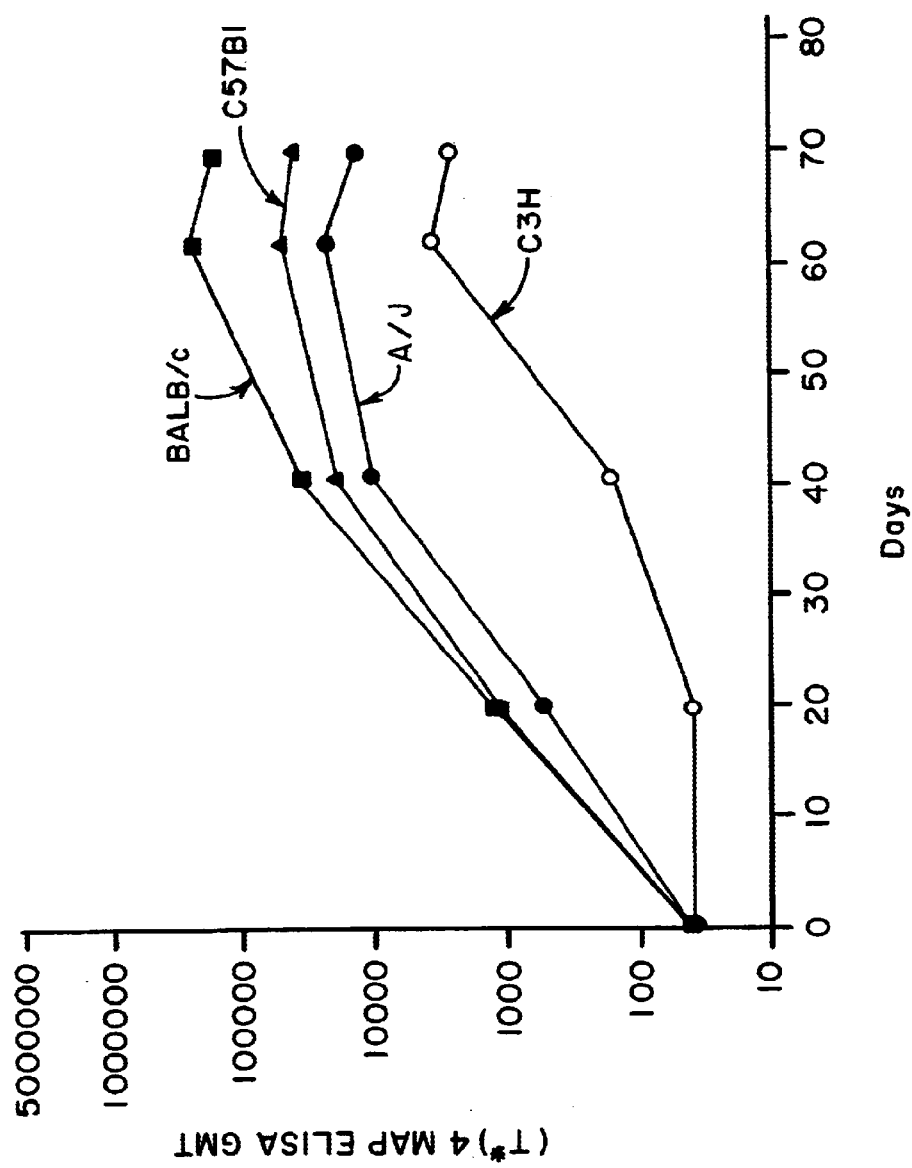

FIG. 4A is a graphic illustration of anti-MAP ELISA titers measured in mice that had been immunized intraperitoneally with 50 μg (T1)$_4$ MAP. FIG. 4B is a graphic illustration of anti-MAP ELISA titers measured in mice that had been immunized intraperitoneally with 50 μg (T*)$_4$ MAP. FIG. 4C is a graphic illustration of anti-MAP ELISA titers measured in mice that had been immunized intraperitoneally with 50 μg (T*T1)$_4$ MAP.

SUMMARY OF THE INVENTION

The present invention encompasses immunogenic compositions that elicit protective immunity against malaria. The compositions comprise a first malaria-derived peptide comprising a "universal" T-cell epitope, which elicits anti-malaria T-cell response in mammals of diverse genetic backgrounds. As used herein, mammals of "diverse genetic backgrounds" include without limitation mammals expressing a multiplicity of MHC class II haplotypes. In one embodiment, the universal T-cell epitope comprises the sequence EYLNKIQNSLSTEWSPCSVT (SEQ ID NO:3). Preferably, the compositions of the invention further comprise at least a second malaria-derived peptide comprising a B-cell epitope, which stimulates the production of anti-malarial antibodies in mammals. The compositions may also comprise additional T-cell epitopes. The compositions are preferably formulated into vaccines, which may also comprise a pharmaceutically acceptable carrier or diluent and, optionally, an adjuvant.

In another aspect, the invention provides methods for inhibiting the propagation of malarial organisms in a susceptible animal, preferably by eliciting protective immunity against malaria in the mammal. The methods are carried out by administering to mammals immunogenically effective amounts of the immunogenic compositions and vaccines described above.

DETAILED DESCRIPTION OF THE INVENTION

All patent applications, patents, and literature references cited in this specification are hereby incorporated by reference in their entirety. In the case of inconsistencies, the present description, including definitions, will control.

Definitions

1. An "immunogenic composition" is a composition that elicits a humoral and/or cellular immune response in a host organism.

2. A "B-cell epitope" as used herein refers to a peptide or other immunogenic molecule, or a fragment thereof, that elicits the production of specific antibodies (i.e., antibodies that recognize the parasite as well as the immunogenic molecule) in a mammalian host. A "T-cell epitope" refers to a peptide or immunogenic molecule, or fragment thereof, that activates T-cells in a manner that is specific for the parasite-derived peptide as well as the immunogenic molecule.

3. A "universal" T-cell epitope as used herein refers to a peptide or other immunogenic molecule, or a fragment thereof, that binds to a multiplicity of MHC class II molecules in a manner that activates T-cell function in a class II- or class I-restricted manner.

The activated T-cells may be helper cells (CD4+) and/or cytotoxic cells (class II-restricted CD4+ and/or class I-restricted CD8+). In one embodiment, the universal T-cell epitope comprises the sequence EYLNKIQNSLSTEWS-PCSVT (SEQ ID NO:1). In another embodiment, the universal T-cell epitope consists essentially of the sequence EYLNKIQNSLSTEWSPCSVT (SEQ ID NO:3). As used herein, an epitope "consisting essentially of" a peptide sequence encompasses peptides in which one or more amino acids may be deleted or substituted while retaining the ability of the peptide to bind to a multiplicity of MHC Class II molecules and/or to activate T-cell function of cells carrying such molecules. It will be understood that deletion or substitution of one or more amino acids may alter the ability of the peptide to bind to one or more MHC Class II molecules but still allow binding to a multiplicity of other MHC Class II molecules.

A malaria-specific or parasite-specific universal T-cell epitope has the potential to expand, or induce, parasite-specific T-cells in naturally-infected and naive individuals, respectively, in the general population.

4. A peptide epitope that is "derived from" a particular organism or from a particular polypeptide comprises an amino acid sequence found in whole or in part within the particular polypeptide and encoded by the genome of the organism. It will be understood that changes may be effected in the sequence of a peptide relative to the polypeptide from which it is derived that do not negate the ability of the altered peptide, when used as part of an immunogenic composition, to elicit an immune response that is specific for the polypeptide from which the peptide is derived.

5. "Multiple Antigen Peptide" (MAP) refers to peptide multimer formed from a polylysine core and containing a branched scaffolding onto which peptides are conjugated (Tam, *J. Immunol.Meth.* 196:17, 1996; Nardin et al., *Adv.Immunol.* 60:105, 1995).

The present invention provides immunogenic compositions and methods for eliciting protective immunity against malaria, in particular against *P. falciparum*. The compositions comprise one or more of the following components: (i) at least one malaria-derived peptide comprising a universal T-cell epitope capable of eliciting an anti-malarial T-cell response in vaccinees of diverse genetic backgrounds; and (ii) at least one malaria-derived peptide comprising a B-cell epitope capable of stimulating the production of anti-malarial (i.e., neutralizing) antibodies directed against the sporozoite stage of the malarial organism. Preferably, the immunogenic compositions of the present invention comprise at least one B-cell epitope and at least one T-cell epitope, most preferably a universal T-cell epitope. The B-cell epitopes preferably elicit the production of antibodies that specifically recognize and bind to the malarial circumsporozoite (CS) protein. The compositions may also comprise B-cell and/or T-cell epitopes derived from, and reactive with, other malarial components, such as, for example, the *P. falciparum* sporozoite surface protein designated Thrombospondin Related Adhesion (Anonymous) protein (TRAP), also called Sporozoite Surface Protein 2 (SSP2); LSA I; hsp70; SALSA; STARP, Hep17; MSA; RAP-1; and RAP-2.

In one embodiment, the B-cell epitope and universal T-cell epitope components are incorporated into multiple antigen peptides (MAPs), forming a synthetic macromolecular polypeptide containing a high density of the epitopes. Methods for MAP synthesis are disclosed in (Tam, *Proc. Natl.Acad.Sci. USA* 85:5409, 1988; Tam, Meth.Enzymol. 168:7, 1989).

The present invention encompasses B-cell and T-cell epitopes derived from plasmodial species, including without limitation *P. falciparum, P. vivax, P. malariae, P. ovale, P. reichenowi, P. knowlesi, P. cynomolgi, P. brasilianum, P. yoelii, P. berghei,* and *P. chabaudi.* Epitopes typically comprise at least 5 amino acid residues, preferably at least 7 residues, and most preferably at least 10 residues, derived from a plasmodial protein. B-cell epitopes may be identified by methods well known in the art, such as, for example, by (i) preparing synthetic peptides whose sequences are derived from the CS protein of a plasmodial species; and (ii) testing the ability of the synthetic peptides to elicit anti-malarial antibodies in a model system. Malaria-specific B-cell and T-cell epitopes are disclosed in Nardin et al., *Ann.Rev.Immunol.* 11:687, 1993.

In one preferred embodiment, the immunogenic composition of the invention comprises a peptide comprising the malarial B-cell epitope (NANP)$_3$ and a peptide comprising the universal T-cell epitope represented by amino acid residues numbered 326–345, EYLNKIQNSLSTEWSPCSVT (SEQ ID NO:3), of the *P. falciparum* NF54 strain CS protein, or immunogenic variants derived therefrom. In another preferred embodiment, the immunogenic composition of the invention comprises (NANP)$_3$, EYLNKIQNSLSTEWSPCSVT (SEQ ID NO:3), and the T1 epitope. Related sequences in other isolates and in other malarial species share an identical pattern of aliphatic and aromatic residues at positions 327, 328, 331, 335, and 339. These residues are thought to represent critical anchors for binding of the peptide within the peptide-binding cleft of class II or class I & molecules. Accordingly, sequences related to EYLNKIQNSLSTEWSPCSVT (SEQ ID NO:3) that share these structural features and/or bind efficiently to different class II or class I molecules may be used in the invention.

Other universal T-cell epitopes for use in the present invention may be identified using the experimental methods described below for EYLNKIQNSISTEWSPCSV (SEQ ID NO:3).

Identification of Universal T-cell Malaria Epitopes

In practicing the present invention, malaria-specific universal T-cell epitopes are identified using one or more of the following methods: (i) experimentally measuring the interaction of different malaria-derived peptides with isolated class II polypeptides in vitro; and (ii) computationally analyzing different peptide sequences to identify high-affinity class II allele-specific motifs. The interactions that have been measured in vitro have been correlated with in vivo immunogenicity, as measured by the immune response of mice of different genetic backgrounds when immunized with multiple antigen peptides (MAP) containing these T-cell epitopes. Similarly, a peptide derived from *P. falciparum* TRAP/SS 2 that was predicted to comprise a universal T-cell epitope has been shown experimentally to bind multiple class II molecules in vitro. These methods for the identification of universal T cell receptors are described in more detail below.

I. In vitro assay:
Mateials and Methods:
  Peptides:
  Synthesis of multiple antigen peptides (MAPs) was carried out as originally described (Tam, *Proc.Natl.Acad.Sci. USA* 85:5409, 1988). Solid-phase stepwise synthesis based on Boc peptide chemistry was used to synthesis the T-cell epitopes on a tetrabranched core constructed using the alpha and epsilon amino groups of lysine. Two mono-epitope MAPs were constructed to contain only the T1 epitope (DPNANPNV)$_2$, SEQ ID NO:4 abbreviated (T1)$_4$, or only the 326–345 T-cell epitope of the CS protein of *P. falciparum* NF54 strain, EYLNKIQNSLSTEWSPCSVT (SEQ ID NO:3, abbreviated (T*)$_4$. A tetrabranched di-epitope MAP containing both the T* and the T1 epitope [T*T1]$_4$, synthesized as a 36-mer sequence with the T* epitope distal to the lysine core, was also constructed.

NH$_2$ terminal biotinylated T1, 326–345 and (NANP)$_3$ peptides were purchased from AnaSpect (Anaheim, Calif.). The peptides were over 90% pure by HPLC and biotinylation of the peptides was confirmed by mass spectrometry.

Mice:
6–8 week old mice of four inbred strains were obtained from Jackson Laboratories, Bar Harbor, Me. Groups of 5–10 mice of A/J (H–2$^a$), C57B1/10 (H–2$^b$), BALB/c (H–2$^d$) and C3H (H–2$^k$) strains were immunized by three intraperitoneal injections of 50 μg mono- or di-epitope MAPs emulsified in Freund's adjuvant. Sera were collected 14–20 days after each immunization for serological assays.

Serological Assays:
ELISA: Enzyme linked immunoadsorbent assay (ELISA) was carried out using mono- or di-epitope MAPs as antigens (Munesingh et al., *Eur.J.Immunol.* 12:3015, 1991). The blocked MAP-coated ELISA wells were incubated with two-fold dilutions of sera in PBS/0.05% Tween/2.5% BSA. After washing, the bound antibody was detected using peroxidase-labelled anti-mouse IgG (γ chain specific) (Kirkegaard and Perry, Gaithersburg, Md.) and ABTS (2,2'-Asino-di-(3-ethylbenzthiazoline sulfonate)/H$_2$O$_2$ as substrate. Geometric mean titers (GMT) were determined for each group using as endpoint the last sera dilution having an O.D. greater than the mean+3 S.D. of pre-immune sera.

IFA: Indirect immunofluorescence (IFA) was carried out using glutaraldehyde-fixed *P. falciparum* sporozoites and FITC-labeled anti-mouse IgG to detect bound antibody. Sporozoites were dissected from the salivary glands of *Anopheles* mosquitoes infected by feeding on *P. falciparum* (NF54 strain) gametocytes derived from in vitro blood stage cultures.

Peptide Binding Assays:

Binding of Peptides to Cells Expressing Defined Class II Molecules:

Binding of biotinylated peptides to EBV-B cells of defined haplotyps, or L cells transfected with DR molecules, was assessed by flow cytometry (Busch et al., *J.Immunol. Meth.* 134:1, 1990). EBV-B cell lines 9065 and 9008, which present peptides to T1 specific CD4+ T-cell clones, were tested for the capacity to bind biotinylated T1, (NANP)$_3$ or 326–345 peptides.

For flow cytometry, EBV-B cells or L cells (2×10$^5$ cells), were incubated with an equal volume (100 μl) of biotinylated peptide (200 μg/ml) in each well of a U-bottomed 96-well plate. Following a 4-hour incubation on ice with gentle agitation, the unbound peptides were removed by washing. To increase the sensitivity of the fluorescent signal, two layers of FITC-Avidin were used to label the cells by incubating first with FITC-Avidin D, followed by biotinylated anti-Avidin D and again FITC-Avidin DCS (Vetor, Burlingame Calif.). Propidium Iodide (2.8 μg/ml) was added prior to FACS analysis to allow gating on viable cells.

Peptide binding ELISA:
Peptide interactions with soluble DR or DQ molecules were measured using a peptide binding ELISA (Hammer et al., *J.Exp.Med.* 180:2353, 1994). The class II molecules were obtained from approximately $10^9$ EBV-B cells by lysis and extraction using 1% NPA40 (v/v) and a cocktail of protease inhibitors. The class II molecules in the cell extracts were purified by immunoaffinity on a Sepharose-Protein A-anticlass II Mab column constructed using Mab specific f or DR (ATCC HB-55) or DQ (ATCC 144 or SPV-L3) molecules.

Homozygous EBV-B cell lines were used as the source of class II molecules for each of the DR peptide competition assays: DR 1-HOM-2 (DRB1*0101), DR 3-WT49 (DRB1*0301), DR4-BSM or PREISS (DRB1*0401), DR 7-EKR (DRB1*0701), DR 8-BM9 (DRB1*0801), DR 11-SWEIG (DRB1*1101) and DR 13-HHKB (DRB1*1301). DR 2a (DRB5*0101) molecules were isolated from L cells transfectant L416.3. The DQ peptide competition assays used soluble DQ 7 molecules (DQA1*0501/DQB1*0301) derived from SWEIG EBV-B cells. DQ 9 $\alpha\beta$ dimers (DQA1*0201/DQB1*0303) were produced in insect cells using the baculovirus expression system.

In the peptide binding assay, an optimal concentration of purified DR or DQ molecules, was added to each well of a 96 well plate along with biotinylated indicator peptide in citrate-phosphate buffer containing 2% n-octyl-glucoside, PMSF, EDTA and protease inhibitors. A binding buffer at pH 7 was used for all the DQ and DR assays, with the exception of the DRB1*0701 binding buffer which was pH 5. Following incubation overnight at room temperature (RT) or 37° C., the peptide/class II complexes were transferred to wells coated with anti-DR Mab L234 antibody (15 $\mu$g/ml) or anti-DQ Mab HB144 (3.5 $\mu$g/ml). Following a two hour incubation, the wells were washed with PBS+1% Tween, and the capture of the biotinylated peptide/class II molecule complexes was revealed by addition of alkaline phosphatase-labelled strepavidin and substrate, p-nitrophenylphosphate (Kierkegaard and Perry, Gaithersburg, Md.). Optical densities were determined in a Titertek MC Multiscan ELISA reader (Flow Labs) using a 405 nm filter.

To increase sensitivity, biotinylated indicator peptides known to bind optimally to the different DR alleles were used in the peptide competition assays. Poly-alanine designer peptides containing allele-specific binding motifs were used as indicator peptides, since these peptides allowed detection of competitors with 100-fold increases or decreases in binding affinity. Biotinylated Gly-Phe-Lys-(Ala)$_7$, SEQ ID NO:5 designated GFK(A)$_7$, was used as indicator peptide in the DR 1, 4, 7 and 13 assays and in DQ assays. The DR 3 assay used biotinylated IAYD(A)$_5$ SEQ ID NO:6 and DR 8 assays utilized a biotinylated GYR(A)$_6$L SEQ ID NO:7 indicator peptide. DR 4 competition assays were also carried out using biotinylated peptide UD 4, YPKFVKQNTIXAA (SEQ ID NO:8), designed for optimal binding to all DR 4 allotypes. Binding to DR 2 (DRB5*0101) molecules was measured using biotinylated peptide of myelin basic protein MBP.

For the peptide competition assays, an optimal concentration of the biotinylated indicator peptide (0.1 $\mu$M–5 $\mu$M) was incubated with tenfold dilutions (0.01 $\mu$M–100 $\mu$M) of the unlabelled competitor peptides, T1, aa 326–345 or (NANP)$_3$. In each competition assay, an unlabelled peptide of defined class II binding specificity was included as a positive control and to allow determination of relative affinity. The ability of the unlabelled competitor peptide to compete with biotinylated indicator peptide for binding to the class II molecule was revealed by measuring optical density (O.D.). Inhibition was calculated as percentage using the formula: 100X1–($\Delta$ O.D. in presence of competitor peptide/$\Delta$ O.D. in absence of competitor). The concentration of competitor peptide required to inhibit 50% of binding of the biotinylated indicator peptide (IC$_{50}$) was determined and IC$_{50}$<100 $\mu$M were taken as indication of peptide binding to the class II molecule.

Results:

Binding of CS T-cell Epitopes to Cell-associated Class II Molecules:

Human CD4+ T-cell clones derived from sporozoite-immunized volunteers recognize T-cell epitopes of the *P. falciparum* CS protein in the context of DR or DQ class II molecules. Clones specific for the 326–345 T-cell epitope (T*) of the *P. falciparum* CS protein are restricted by multiple DR alleles, including DR 1, DR 4, DR 7, or DR 9. The genetic restriction of the T1 epitope, located in the repeat region of the *P. falciparum* CS protein, has recently been defined. Monoclonal antibodies specific for monomorphic determinants of DQ, but not DR molecules significantly inhibited the proliferative response of the T1 peptide-specific T-cell clones. When EBV-B cells expressing the DR/DQ haplotype of the sporozoite-immunized T-cell donor (DRB1*1502/*1301, DQB1*0602/*0603) were used as APC, only cells expressing DQB1*0603 could present the T1 peptide to the T-cell clones.

However, the number of CS peptide specific T-cells available for the study of genetic restrictions has been limited by the small number of sporozoite-immunized volunteers. To obtain additional information on the range of class II molecules that could potentially function in presentation of the T1 and 326–345 T-cell epitopes, in vitro binding assays were carried out using cell lines of defined haplotypes or DR transfectants.

a. Binding Assays Using EBV-B Cells of Defined Class II Haplotypes

To determine whether EBV-B of known haplotypes could be used to screen for molecules capable of binding the CS epitopes, cell lines were tested for binding of biotinylated T1 SEQ ID No: 4 and 326–345 SEQ ID No: 3 peptides. The biotinylated (NANP)$_3$ SEQ ID No: 1 peptide, known to be poorly recognized by human T-cells, was also tested. Two EBV-B cell lines, one expressing DR 4 (BSM) and one expressing DR 7 (EKR), were known to function as APC for the presentation of the 326–345 peptide to DR4 and DR 7 restricted T-cell clones. As measured by flow cytometry, the biotinylated 326–345 peptide bound to the BSM and EKR cell lines with mean fluorescent channels (MFC) of 251 and 142, respectively. However, no detectable binding of the T1 epitope or the biotinylated (NANP)$_3$ peptide to these cells was obtained (MFC<35).

Figure 1B:
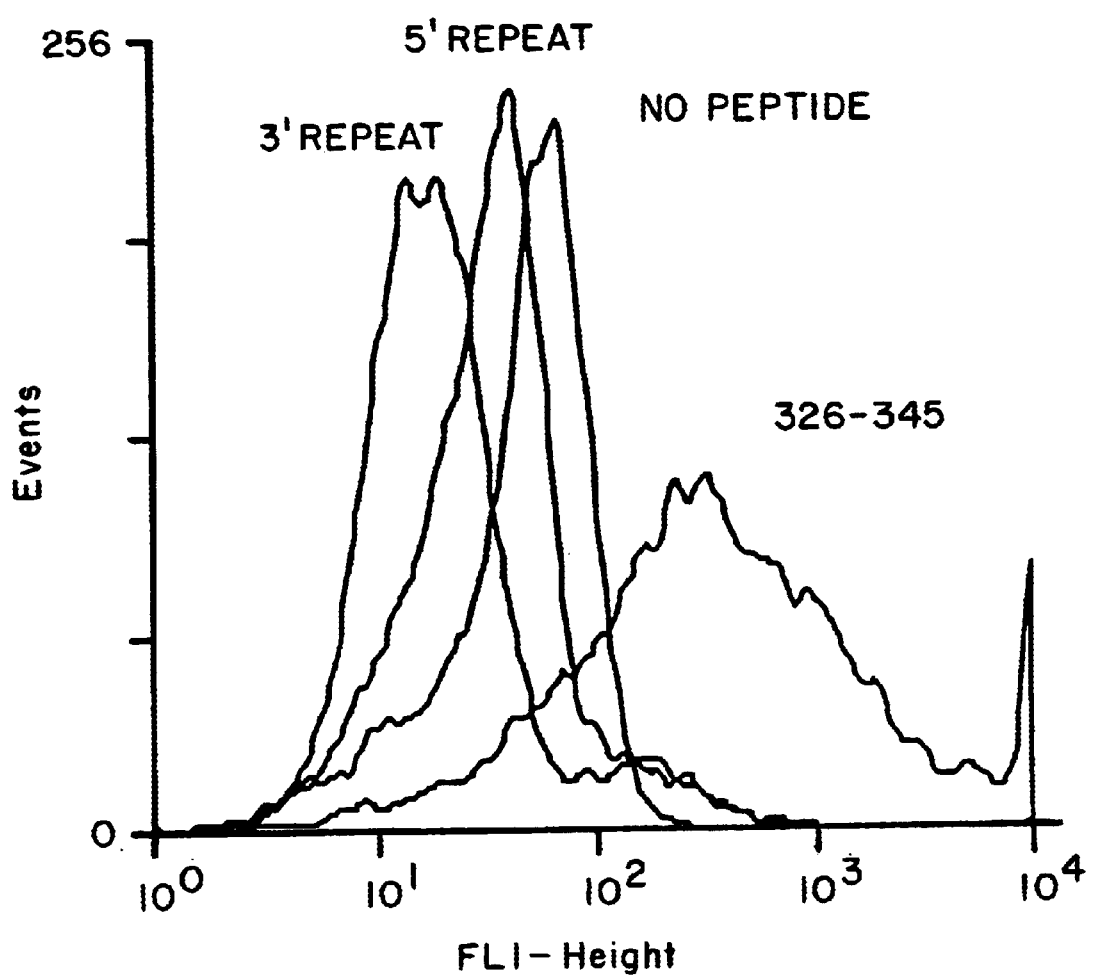

In the converse assays, EBV-B cell lines known to function as APC for the T1 peptide-specific T-cell clones were tested for their ability to bind detectable levels of the biotinylated CS peptides. Binding of the biotinylated T1 peptide to EBV-B cell lines 9008 and 9065, which express DRB1*1501/DQB1*0602/0603 and the DRB1*1301/DQB1*0603 haplotypes, could not be detected (FIGS. 1A and 1B). In contrast, the 326–345 peptide bound to both of these EBV-B cells (9008 or 9065) with a MFC of 403 and 758, respectively.

b. Peptide Binding to DR-transfected L Cells

Since EBV-B cells express multiple class II isotypes, positive fluorescence obtained with the 326–345 peptide could reflect binding to either DR and/or DQ, or other HLA molecules. The class II specificity of peptide binding was determined by measuring interaction of the biotinylated CS peptides with DR-transfected L cells.

The level of expression of DR on the surface of the different transfectants was comparable to that observed on EBV-B cells, with MFC ranging from 443 to 964 following staining with anti-DR (L243) monoclonal antibodies (Table 1).

TABLE 1

Binding of biotinylated malaria peptides to DR transfected murine L cells

| Biotinylated Peptide | DR TRANSFECTANTS (MFC[a]) | | |
|---|---|---|---|
| | DRB1*0401 | DRB1*0701 | DRB1*1501 |
| Biotinyl-326-345 | 217.1 | 203.8 | 167.7 |
| Biotinyl-T1 | 18.9 | 35.7 | 12.7 |
| Biotinyl-(NANP)$_3$ | 12.9 | 22.8 | 12.7 |
| Anti-DR Mab[b] | 911.4 | 443.5 | 964.4 |
| Control Mab | 18.5 | 23.8 | 19.3 |

[a]Binding of biotinylated CS peptides (100 μg/ml) to murine L cells transfected with DRA1*0101 and DRB1*0401, *0701 or *1501 genes was measured by FACS. Results expressed as mean fluorescence channel (MFC).
[b]Class II expression on each of the transfectants was demonstrated by staining with Mab specific for human class II molecules (Mab L234) or a negative control Mab (3D11) (50 ug/ml).

No significant fluorescence was obtained when the biotinylated T1 peptide, or the (NANP)$_3$ peptide, was incubated with the DR transfected cell lines. The biotinylated 326–345 peptide bound to the cells transfected with DRB1*0401 and *0701 with MFC of 217 and 203, respectively, consistent with the allele specificity of the DR4- and DR7-restricted CD4+ T-cell clones specific for the 326–345 peptide. In addition, the 326–345 peptide was also shown to bind to DR B1*1501 transfected L cells (MFC 167), consistent with the positive binding observed with the DR15 positive 9008 EBV-B cell line (FIG. 1A).

Binding of CS T-cell Epitopes to Soluble Class II Molecules

In order to measure peptide binding affinity and to rule out non-specific interactions with non-MHC cell surface molecules expressed on the human and murine cell lines, peptide competition binding assays using soluble class II molecules were carried out.

1. DR Molecules

To increase the sensitivity and specificity of the peptide binding assays, competition assays were carried out using a biotinylated indicator peptide GFK(A)$_7$, a polyalanine peptide that binds to DR molecule with an affinity permitting competition by peptides with 100 fold range of affinities. As shown by the dose response curve for various concentrations of cold competitor peptide, the 326–345 peptide, but not the T1 or (NANP)$_3$ peptide, could effectively inhibit the binding of the biotinylated GFK(A)$_7$ indicator peptide, to soluble DR4 molecules (FIG. 2A).

Similar results were obtained when the 326–345 peptide was tested in the peptide competition assay using soluble DR13 molecules (FIG. 2B). The concentration of 326–345 peptide required to inhibit 50% of binding of the biotinylated GFK(A)$_7$ peptide (IC$_{50}$) was comparable in both the DR 4 (IC$_{50}$ 0.2 μM) and the DR 13 (IC$_{50}$ 0.33 μM) peptide competition assays. Neither the T1 peptide, nor the (NANP)$_3$ peptide, gave detectable inhibition at the highest concentration tested (IC$_{50}$>100/μM).

The results of a series of peptide binding competition assays, carried out using different biotinylated indicator peptides selected for optimal binding to each DR allele, are summarized in Table 2.

TABLE 2

Peptide Binding Competition Assay using soluble DR molecules

| DR[a] | DRB1* | Biotinyl-peptide | Competitor Peptide IC$_{50}$ | | | |
|---|---|---|---|---|---|---|
| | | | HA$_{307-319}$ | 326-345 | T1 | (NANP)$_3$ |
| DR 1 | DRB1*0101 | GFK(A)$_7$ | 0.10 | 20.0 | >100 | >100 |
| DR 2 | DRB5*0101 | MBP | 0.03 | 80.0 | >100 | >100 |
| DR 3 | DRB1*0301 | IAYD(A)$_5$ | 10.00 | 70.0 | >100 | >100 |
| DR 4 | DRB1*0401 | UD4 | 1.00 | 0.7 | >100 | >100 |
| DR 7 | DRB1*0701 | GFK(A)$_7$ | 0.10 | 0.4 | >100 | >100 |
| DR 8 | DRB1*0801 | GYR(A)$_6$L | 5.00 | 10.0 | >100 | >100 |
| DR 11 (5) | DRB1*1101 | TT$_{831-843}$ | 1.00 | 40.0 | >100 | >100 |

[a]Results are expressed as IC$_{50}$, the concentration (μM) of unlabelled competitor peptide required to inhibit 50% of the binding of a biotinylated indicator peptide. The percent inhibition was calculated based on O.D. obtained in the presence of different concentrations of competitor peptide (100–0.001 μM). An IC$_{50}$ < 100 μM indicates positive peptide binding.

A known positive competitor peptide derived from influenza hemagglutinin, HA$_{307-319}$, was included in each assay in order to determine the relative affinity of binding of the CS peptides to each DR allele.

Based on these assays, the 326–345 peptide could be shown to bind to DRB1* gene products encoding DR 1, DR 4, DR 7, DR 8, DR 11 and DR 13 class II molecules (FIG. 2, Table 2). The 326–345 peptide was a weak competitor for binding to DR 3 molecules (IC$_{50}$ 70 μM) and to DR 2a molecules, encoded by DR B5*0101(IC$_{50}$ 80 μM).

Significant binding of the T1 peptide, or the (NANP)$_3$ peptide, was not detected with any of the soluble DR molecules tested in the peptide binding assays (IC$_{50}$>100 μM).

The affinity of binding of the 326–345 peptide was different for each DR allele as determined by the IC$_{50}$ and the relative affinity when compared with the HA$_{307-319}$ peptide. In the case of DR 4,7, 8 alleles, binding of the 326–345 CS peptide was comparable to the universal HA peptide, with IC$_{50}$ HA$_{307-319}$/CS$_{326-345}$ ratios of 1.4, 0.25 and 0.5, respectively. However, the relative affinity of binding of the 326–345 peptide to DR 1 and DR 11 was lower, with IC$_{50}$ ratios of 0.005 and 0.025.

2. DQ Molecules

The results of the DR binding assays indicated that the 326–345 peptide could bind to multiple DR molecules, while the T1 peptide and the (NANP) peptide did not bind with high affinity to any of the DR molecules tested. To determine whether the DQ 6-restricted T1 epitope could bind to other DQ alleles, peptide competitions using soluble DQ molecules were carried out.

Peptide competition assays used soluble DQ 7 (DQA1*0501/B1*0301) and DQ 9 (DQA1*0201/B1*0303) molecules were established. A known DQ binding peptide, $CLIP_{83-101}$, derived from aa 83–101 of the Invariant chain, was included in each assay to determine the relative affinity of binding of the CS peptides to soluble DQ molecules.

The T1 peptide, which was known to bind to DQ 6 molecules, did not bind to either the DQ 7 or DQ 9 molecules (FIG. 3). Similarly, the $(NANP)_3$ peptide did not compete with the $CLIP_{83-101}$ peptide for binding to either DQ allele.

In contrast, the 326–345 peptide, could compete with CLIP peptide for binding to DQ molecules. In the competition assay using soluble DQ 9 molecules, the 326–345 peptide gave an $IC_{50}$ of 2 $\mu M$, a binding affinity in the range of that obtained with the $CLIP_{83-101}$ peptide ($IC_{50}$ 0.5 $\mu M$) (FIG. 3A). Binding of 326–345 peptide was also detected with soluble DQ 7 molecules ($IC_{50}$ 20 $\mu M$), although the affinity of the peptide/DQ interaction was weak compared with the CLIP peptide ($IC_{50}$ 0.5 $\mu M$) (FIG. 3B).

Immunogenicity of synthetic peptide vaccines containing T*T1 epitopes:

a. Immunization With Mono-epitope MAP Containing CS T-cell Epitopes

The results of the peptide binding assays demonstrated that the 326–345 peptide could bind to a broad range of class II molecules, while the T1 peptide showed detectable binding only to the DQ 6 molecule in the T-cell assays. In order to determine whether the broad versus limited genetic restrictions of the 326–345 and the T1 peptides correlated with immunogencity in vivo, the immune response to multiple antigen peptides (MAPs) containing either the 326–345, or the T1, epitope was determined in different strains of mice. Preliminary studies had determined that the 326–345 epitope contained B-cell, as well as T-cell epitopes, and therefore the anti-MAP antibody response was used as an indicator of functional class II restricted T helper cells in the MAP immunized mice.

Consistent with the binding of the 326–345 peptide to multiple class II molecules in vitro, mono-epitope MAP containing only the 326–345 sequence (abbreviated T*) elicited anti-peptide responses in all four strains of mice tested (FIG. 4B). The magnitude of the response was genetically restricted, with high levels of anti-peptide antibody obtained in BALB/c ($H-2^d$) and C57B1 ($H-2^b$) and intermediate levels in A/J ($H-2^a$) mice. All the mice in the high and intermediate responder strains developed similar levels of anti-peptide antibody following immunization with the 326–345 MAP (SEM<10%). However, lower, more variable antibody responses were obtained in the C3H ($H-2^k$) in which only 2/5 MAP immunized mice responded with detectable antibody levels.

In contrast, to the response to the $(T^*)_4$MAP containing the 326–345 epitope, monoepitope MAP containing the T1 epitope elicited anti-peptide antibody responses in only a single strain of mice, $H-2^b$ (FIG. 4A), consistent with previously published results (36). The genetic restriction of the murine response to the $NH_2$-terminal repeat T1 epitope is therefore the same as that observed for the COOH-terminal repeat (NANP) sequence, with T helper cell epitopes recognized only by the C57B1 ($H-2^b$) mice.

To determine whether the anti-peptide antibodies elicited by MAPs containing the repeat T1, or the COOH-terminal 326–345 sequence, could recognize CS protein on the *P. falciparum* sporozoite, indirect immunofluorescence assays (IFA) were carried out. It had previously been found that immunization with MAPs constructs containing COOH-terminal sequences of the *P. falciparum* CS protein frequently elicited high levels of anti-peptide antibodies that failed to react with sporozoites. Consistent with these earlier findings, only anti-MAP antibodies that recognized the repeat region of the CS protein were reactive with sporozoites. Therefore, while the BALB/c mice immunized with the $(T^*)_4$ developed the highest titers of anti-326–345 antibodies (ELISA GMT 163,840), no reactivity with *P. falciparum* sporozoites (IFA<80) was detected. In contrast, the single mouse strain, C57B1, that responded to immunization with the mono-epitope $(T1)_4$ MAP containing the $NH_2$-terminal repeat T-cell epitope (FIG. 3A), gave comparable anti-T1 peptide ELISA titers (GMT 327,680) and IFA titers with *P. falciparum* sporozoites (163,840).

b. Immunization With Di-epitope MAPs

The results of the peptide binding assays and the immunogenicity studies in the different strains of mice demonstrate that the 326–345 peptide can be recognized by multiple human and murine class HI molecules. To determine whether the inclusion of the 326–345 T-cell epitope in a synthetic vaccine could overcome the genetic restriction of the immune response to the repeat region of the *P. falciparum* CS protein, a di-epitope $(T^*T1)_4$ MAP was synthesized containing the 326–345 epitope SEQ ID NO:3 in tandem with the T1 epitope SEQ ID NO:4, the T*T1diepitope being defined by SEQ ID NO:9.

The anti-MAP antibody response in the mice immunized with the $(T^*T1)_4$ MAP demonstrates that, as was found with the mono-epitope $(T^*)_4$ MAP, all four strains of mice responded to immunization and produced high levels of anti-peptide antibodies (FIG. 4C). The magnitude of the anti-$(T^*T1)_4$ MAP antibody response in the different strains demonstrated the same hierarchy as that obtained in mice immunized with the mono-epitope $(T^*)_4$ MAP, i.e. BALB/c, C57B1>A/J>C3H.

The kinetics of the anti-MAP antibody response were more rapid in the di-epitope immunized mice (FIG. 4C). Anti-MAP titers exceeding $10^5$ could be detected following a single dose of $(T^*T1)_4$ MAP in the C57B1 mice. The lowest antibody titers were noted with the C3H mice; however, in contrast to mice immunized with the mono-epitope AP, all the mice immunized with the di-epitope $(T^*T1)_4$ MAP developed anti-MAP antibodies.

More importantly, the analysis of the fine specificity of the antibody responses demonstrated that all strains of mice immunized with the $(T^*T1)_4$ MAP developed antibody reactive with *P. falciparum* sporozoites (Table 3). As noted with previous MAP constructs containing repeats of *P. falciparum* CS protein, there was a positive correlation between the level of anti-repeat antibodies, as measured by $(T1)_4$ MAP ELISA, and reactivity with *P. falciparum* sporozoites in the sera of the di-epitope MAP immunized mice.

TABLE 3

Fine specificity of antibodies elicited by immunization with di-epitope (T*T1)₄ MAP

| STRAIN | (T*T1)₄ ELISA | (T*)₄ ELISA | (T)₄ ELISA | IFA |
|---|---|---|---|---|
| BALB/C | 1,558,718 | 48,710 | 115,852 | 163,840 |
| C57BL | 702,398 | 31,042 | 100,855 | 133,079 |
| A/J | 327,680 | 1,810 | 40,960 | 27,024 |
| C3H | 94,101 | 452 | 1,470 | 3,225 |

Results are shown as GMT for sera obtained +28 days post third i.p. injection of (T*T1)₄ MAP in Freund's adjuvant. ELISA were carried out using the di-epitope or mono-epitope MAPs as antigen. IFA were based on glutaraldehyde-fixed *P. falciparum* (NF54) sporozoites.

The magnitude of the anti-repeat and anti-sporozoite antibodies elicited in the different murine strains reflected the pattern of genetic restriction of the 326–345 epitope. The high (C57B1, BALB/c, A/J) and low (C3H) responders to the mono-epitope (T*)₄ MAP were also high and low responders in the production of anti-sporozoite antibodies following immunization with di-epitope MAP.

Vaccines

The compositions of the present invention may be used as immunogens to elicit immunity, including protective immunity, in a susceptible host. Immunity may include eliciting the production of antibodies in the host (or in another host or in vitro, as in passive immunization) that will recognize and bind to plasmodial cells. Immunity may also include the activation of malaria-specific T-cells. Thus, the immunogenic compositions comprising universal T-cell epitopes may be used in vaccine preparations to confer prophylactic or therapeutic immunity by preventing (totally or partially) propagation of the disease in the host, such as, e.g., by inhibiting development of the pre-erythrocytic stages of the organism.

It should be noted that 100% inhibition of any stage in malarial infection or propagation by an immunogenic composition (or by vaccine containing it, or by an antibody) is not necessary for these materials to be useful. Any substantial decrease in the extent of infection (as measured, e.g. by the extent of parasitemia) would substantially attenuate the clinical symptoms and substantially increase the probability for survival and recovery of the host.

There are many protocols for the preparation of vaccines known in the art. Typically, vaccines are prepared as injectables, either as liquid solutions or suspensions. Solid forms suitable for dissolving or suspending in liquid prior to injection may also be prepared. The preparation may also be emulsified, or the protein encapsulated in liposomes. The active immunogenic ingredients may be mixed with excipients, such as, for example, water, saline, dextrose, glycerol, ethanol, or the like, and combinations thereof. In addition, if desired, the vaccine may contain minor amounts of auxiliary substances such as wetting or emulsifying agents, pH buffering agents, and/or adjuvants to enhance the effectiveness of the vaccine. The immunogenic compositions could also be administered following incorporation into liposomes or other microcarriers.

Repeat immunizations may be necessary to enable the host to mount an immune response. Both amounts of immunogen and immunization protocols can be determined experimentally, as is well-known in the art, using animal (e.g. primate) models followed by clinical testing in humans. Information on vaccine compositions and immunization is described for example in U.S. Pat. No. 4,767,622 of Ristic (Aug. 30, 1988); U.S. Pat. No. 4,735,799 of Patarroyo (Apr. 5, 1988) and Patarroyo, M. E., et al., Nature 332:158, 1988; and published European Application A₁ 250,261 (published Dec. 23, 1987) of the Wellcome Foundation.

The vaccines may be administered by subcutaneous, intramuscular, oral, intradermal, or intranasal routes. Dosages may range from about 5 μg to about 5 mg per dose, and a single or multiple dosage regimen may be utilized. The amounts administered, number of administrations, and schedule of administrations can be determined empirically, such as, for example, by establishing a matrix of dosages and frequencies and comparing a group of experimental units or subjects to each point in the matrix.

The present invention also provides methods of inhibiting the propagation of a malarial organism in a susceptible mammal, which comprises administering to the mammal an immunogenically effective amount of an immunogenic composition comprising one or more of the following components: (i) at least one malaria-derived peptide containing a B-cell epitope capable of stimulating the production of anti-malarial (i.e., neutralizing) antibodies directed against the sporozoite stage of the organism; and (ii) at least one malaria-derived peptide that encompasses a universal T-cell epitope capable of eliciting an anti-malarial T-cell response in vaccinates of diverse genetic backgrounds. An immunogenically effect amount is an amount effective to elicit protective immunity against the malarial organism determined as described above. In a further aspect, the composition may be administered to a mammal which has been previously exposed to the malarial organism. In a still further aspect, the polypeptide may be administered to a mammal prior to exposure of the mammal to the malarial organism.

The following examples are intended to serve as a non-limiting illustration of the present invention.

Example 1

Anti-Malarial Vaccines Comprising MAPs

Studies in mice of different genetic backgrounds have shown that peptide-based vaccines containing the T* epitope (see above) are immunogenic in the absence of adjuvant, i.e., when administered in phosphate buffer alone.

Enhanced antibody responses were obtained by the addition of adjuvants, such s alum (Rehydragel, Reheis N.J.) or QS21 (Cambridge Biotech, Cambridge Mass.).

A typical anti-malarial vaccine comprising MAPs contains 1 mg (T*T1B)₄ MAP mixed with 100 μg QS21. This vaccine is administered by subcutaneous injection.

Example 2

Elicitation of CS-Specific Antibodies in Humans

The following study was performed to examine the effect of immunization with a universal T-cell epitope-containing vaccine on humans of diverse genetic backgrounds.

Methods: A polyoxime synthetic malaria vaccine, termed (T1BT*)₄-P3C, was synthesized. The vaccine contains the universal T-cell epitope (T*) described above in combination with a 28-residue repeated sequence derived from the *P. falciparum* CS repeats, (DPNANPNV)₂(NANP)₃ termed T1B) SEQ ID NO:10. The vaccine also contained a covalently linked synthetic adjuvant, tri-palmitoyl cysteine (Pam3Cys), linked to the lysine core. Methods for synthesis of immunogenic polyoxime compositions in general are disclosed in International Patent Application WO 94/25071. Methods for synthesis of T*-containing polyoximes are disclosed in co-pending application Ser. No. 08/998,335 filed Dec. 24, 1997, now abandoned, based on provisional application Ser. No. 60/034,506, filed Dec. 24, 1996.

The vaccine was administered subcutaneously, without additional adjuvant or emulsifiers, to ten human volunteers who express a broad range of Class II haplotypes (Table 4). Vaccination was on day 0 and day 28. Sera were obtained prior to immunization, on day 14, and on day 42.

Antibody titers were determined using an enzyme-linked immunosorbent assay (ELISA) using plates coated with either the tri-epitope SEQ ID NO:11 polyoxime immunogen (T1BT*)$_4$ or a di-epitope SEQ ID NO:10 MAP containing only the CS repeats (T1B)$_4$. The plates were incubated with two-fold serial dilutions of sera (beginning with 1:80 dilutions), after which the plates were washed and reacted with peroxidase-labelled anti-human IgG. The presence of bound antibody was revealed by addition of a peroxidase substrate (ABTS) and measuring the optical density (OD) at 410 nm. Endpoint titers represent the final dilution of immune sera in which the O.D. was greater than the mean O.D.+3 standard deviations obtained with sera of the ten volunteers prior to vaccination.

Results: As shown in Table 4, at 14 days after a single dose of vaccine, antibodies specific for the polyoxime immunogen could be detected in 50% of the vaccinees. The administration of a second dose of polyoxime vaccine on day 28 increased the anti-peptide antibody responses and positive reactions were detected in the sera of the majority of the vaccinees. Furthermore, antibodies were detected that reacted specifically with the CS repeats, as demonstrated by ELISA carried out using the (T1B)4 MAP. The repeat region of the *P. falciparum* CS protein is the target of protective antibodies which can neutralize infectivity of sporozoites by blocking invasion of host hepatocytes and preventing initiation of the malaria life cycle in the mammalian host. Finally, all of the individuals had positive IgM responses following the second dose of vaccine.

TABLE 4

Immunogenicity of polyoxime vaccine containing the T* *P. falciparum* universal T cell epitope in volunteers of diverse HLA haplotypes.

| Volunteer Number | HLA haplotype | Primary Response | | Secondary Response | |
| --- | --- | --- | --- | --- | --- |
| | | (T1BT*)4 ELISA | (T1B)4 ELISA | (T1BT*)4 ELISA | (T1B)4 ELISA |
| 03 | DR 7, 11 | <80 | <80 | <80 | <80 |
| 04 | DR 11, 15 | 160 | <80 | 2,560 | >1,280 |
| 05 | DR 4, 13 | N.S. | N.S. | 320 | 320 |
| 06 | DR 8, 15 | <80 | <80 | 80 | <80 |
| 07 | DR 3, 7 | 80 | <80 | 80 | <80 |
| 08 | DR 14, 16 | 160 | <80 | 1,280 | 640 |
| 09 | DR 4,15 | 320 | 320 | >2,560 | >1,280 |
| 10 | DR 4, 7 | <80 | <80 | >1,280 | >1,280 |
| 14 | DR 3, 4 | 160 | <80 | 640 | 160 |
| 15 | DR 3, 4 | <80 | <80 | 640 | 320 |

[a]Primary IgG antibody responses were measured in sera collected +14 days after subcutaneous injection of 1 mg (T1BT*)4 polyoxime vaccine. Secondary IgG antibody responses were measured in sera collected +14 days after a second injection of vaccine administered on day 28.

These results indicate that a vaccine containing the universal T cell epitope is capable of eliciting IgG or IgM anti-repeat antibodies specific for the *P. falciparum* CS protein in all of the vaccinees. Thus the inclusion of this universal epitope overcomes the genetic restriction of the immune response to the CS repeats and provides a synthetic peptide vaccine that is immunogenic in individuals of diverse genetic backgrounds.

What is claimed is:

1. An immunogenic composition which comprises a first peptide comprising a universal T-cell epitope, wherein said universal T-cell epitope:

(a) is a sequence of contiguous amino acids as present in a sequence of a circumsporozoite (CS) protein of a plasmodial species, said epitope sequence (i) having a length and alignment of a motif of aliphatic and aromatic amino acid residues which are identical to the length and alignment of the motif of amino acid residues in positions corresponding to residues 2, 3, 6, 10, and 14 of a sequence EYLNKIQNSLSTEWSPCSVT (SEQ ID NO:3) or (ii) corresponding in length and alignment to SEQ ID NO:3 as present in *P. falciparum* NF54 strain CS protein;

(b) is not contiguous in the first peptide with any amino acid sequence which is immediately adjacent to the sequence of the epitope in the sequence of the CS protein of the plasmodial species; and (c) binds many diverse major histocompatability complex (MHC) Class II molecules; wherein said composition elicits an anti-CS parasite-specific T-cell response in humans of diverse human leukocyte antigen (HLA) genetic backgrounds.

2. The immunogenic composition as defined in claim 1, wherein said universal T-cell epitope sequence is contained within the sequence of the circumsporozoite (CS) protein of a plasmodial species selected from the group consisting of *P. falciparum*, *P. vivax*, *P. malariae*, and *P. ovale*.

3. The immunogenic composition as defined in claim 1, wherein said first peptide is incorporated into a multiple antigen peptide (MAP).

4. The immunogenic composition as defined in claim 1, further comprising a second malaria-derived peptide comprising a B-cell epitope which elicits production of antimalarial antibodies in humans.

5. The immunogenic composition as defined in claim 4, wherein said B-cell epitope comprises a sequence (NANP)$_3$ (SEQ ID NO:1).

6. The immunogenic composition as defined in claim 4 wherein said first and second peptides are incorporated into a multiple antigen peptide (MAP).

7. The immunogenic composition as defined in claim 1, further comprising a peptide comprising a plasmodial T1 epitope, (DPNANPNV)$_2$ (SEQ ID NO:4).

8. The immunogenic composition as defined in claim 1, wherein said universal T-cell epitope sequence consists essentially of the sequence EYLNKIQNSLSTEWSPCSVT (SEQ ID NO:3).

9. The immunogenic composition as defined in claim 1, wherein the sequence of the universal T-cell epitope is EYLNKIQNSLSTEWSPCSVT (SEQ ID NO:3).

10. The immunogenic composition as defined in claim 9, wherein said first peptide is incorporated into a multiple antigen peptide (MAP).

11. The immunogenic composition as defined in claim 9, further comprising a peptide comprising a plasmodial T1 epitope, (DPNANPNV)$_2$ (SEQ ID NO:4).

12. The immunogenic composition as defined in claim 9, further comprising a second malaria-derived peptide comprising a B-cell epitope which elicits production of anti-malarial antibodies in humans.

13. The immunogenic composition as defined in claims 12, wherein said B-cell epitope comprises a sequence (NANP)$_3$ (SEQ ID NO:1).

14. The immunogenic composition as defined in claim 12 wherein said first and second peptides are incorporated into a multiple antigen peptide (MAP).

15. A method for eliciting an anti-malarial immune response in a human population of diverse HLA genetic backgrounds, which comprises administering to said population an immunogenically effective amount of the immunogenic composition of claim 9.

16. A vaccine comprising the immunogenic composition as defined in claim 9 and a pharmaceutically acceptable carrier or diluent.

17. The vaccine as defined in claim 16, further comprising a pharmaceutically acceptable adjuvant.

18. A method for inhibiting propagation of a malarial organism in a human, which comprises administering to said human an immunogenically effective amount of the vaccine as defined in claim 16.

19. A method for eliciting an immune response against malaria in a human, which comprises administering to said human an immunogenically effective amount of the vaccine as defined in claim 16.

20. A method for eliciting an anti-malarial immune response in a human population of diverse HLA genetic backgrounds, which comprises administering to said population an immunogenically effective amount of the immunogenic composition of claim 1.

21. A vaccine comprising the immunogenic composition as defined in claim 1, and a pharmaceutically acceptable carrier or diluent.

22. The vaccine as defined in claim 21, further comprising a pharmaceutically acceptable adjuvant.

23. A method for inhibiting propagation of a malarial organism in a human, which comprises administering to said human an immunogenically effective amount of the vaccine as defined in claim 21.

24. A method for eliciting an anti-malarial immune response in a human, which comprises administering to said human an immunogenically effective amount of the vaccine as defined in claim 21.

* * * * *